United States Patent
Hool et al.

(10) Patent No.: US 11,484,713 B2
(45) Date of Patent: Nov. 1, 2022

(54) IN-EAR ELECTRODE ASSEMBLY FOR NON-INVASIVE VAGUS NERVE STIMULATION

(71) Applicant: ARIZONA BOARD OF REGENTS ON BEHALF OF ARIZONA STATE UNIVERSITY, Scottsdale, AZ (US)

(72) Inventors: Nick Hool, Tempe, AZ (US); William J Tyler, Newton, MA (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 106 days.

(21) Appl. No.: 16/642,750

(22) PCT Filed: Aug. 31, 2018

(86) PCT No.: PCT/US2018/049157
§ 371 (c)(1),
(2) Date: Feb. 27, 2020

(87) PCT Pub. No.: WO2019/046757
PCT Pub. Date: Mar. 7, 2019

(65) Prior Publication Data
US 2021/0077812 A1    Mar. 18, 2021

Related U.S. Application Data

(60) Provisional application No. 62/633,692, filed on Feb. 22, 2018, provisional application No. 62/552,764, filed on Aug. 31, 2017.

(51) Int. Cl.
*A61N 1/36* (2006.01)
*A61N 1/02* (2006.01)
(Continued)

(52) U.S. Cl.
CPC ......... *A61N 1/36036* (2017.08); *A61N 1/025* (2013.01); *A61N 1/0456* (2013.01); *A61N 1/37211* (2013.01)

(58) Field of Classification Search
CPC .. A61N 1/36036; A61N 1/025; A61N 1/0456; A61N 1/37211; A61N 1/36053
See application file for complete search history.

(56) References Cited

U.S. PATENT DOCUMENTS

| | | |
|---|---|---|
| 4,966,164 A | 10/1990 | Colsen et al. |
| 8,249,711 B2 | 8/2012 | Libbus et al. |

(Continued)

FOREIGN PATENT DOCUMENTS

| | | |
|---|---|---|
| WO | 2010009141 A1 | 1/2010 |
| WO | 2011057028 A1 | 5/2011 |

(Continued)

OTHER PUBLICATIONS

Notification of Transmittal of the International Search Report and the Written Opinion (Form PCT/ISA/220), International Search Report (Form PCT/ISA/210), and Written Opinion of the International Searching Authority (Form PCT/ISA/237) for International Application No. PCT/US2018/049157 dated Oct. 19, 2018, 10 pages.

(Continued)

*Primary Examiner* — Lynsey C Eiseman
*Assistant Examiner* — Natasha Patel
(74) *Attorney, Agent, or Firm* — Withrow & Terranova, P.L.L.C.; Vincent K. Gustafson

(57) ABSTRACT

Disclosed herein are an electrode assembly, an in-ear headphone, an in-ear headphone pair, and an electrode pair assembly, each for non-invasive vagus nerve stimulation. Each of the foregoing items includes a first electrode and a second electrode. An electrode assembly configured for (Continued)

insertion into an ear of a user includes a first electrode, a second electrode, and a shim positioned therebetween. An in-ear headphone or headphone pair may include the electrode assembly with a housing and a waveform generator. An electrode pair assembly may include a first electrode configured for insertion into a first ear of a user, and a second electrode configured for insertion into a second ear of the user. Certain embodiments further include audio components positioned within a housing of at least one in-ear headphone to deliver audio stimulation through a central channel of a first electrode or second electrode, respectively.

21 Claims, 10 Drawing Sheets

(51) Int. Cl.
*A61N 1/04* (2006.01)
*A61N 1/372* (2006.01)

(56) References Cited

U.S. PATENT DOCUMENTS

| | | | |
|---|---|---|---|
| 8,591,419 B2 | 11/2013 | Tyler | |
| 8,858,440 B2 | 10/2014 | Tyler | |
| 9,403,038 B2 | 8/2016 | Tyler | |
| 10,556,132 B2 | 2/2020 | Tyler | |
| 2006/0122675 A1 | 6/2006 | Libbus et al. | |
| 2010/0057154 A1 | 3/2010 | Dietrich et al. | |
| 2010/0198318 A1* | 8/2010 | Rogers | A61F 7/007 607/99 |
| 2011/0166624 A1 | 7/2011 | Dietrich et al. | |
| 2011/0230938 A1 | 9/2011 | Simon et al. | |
| 2013/0150653 A1 | 6/2013 | Borsody | |
| 2015/0018925 A1* | 1/2015 | Zschaeck | A61N 1/36036 607/139 |
| 2015/0360030 A1* | 12/2015 | Cartledge | A61N 1/0456 607/60 |
| 2016/0250464 A1 | 9/2016 | Zschaeck et al. | |
| 2016/0346117 A1 | 12/2016 | Rogers et al. | |
| 2017/0087364 A1* | 3/2017 | Cartledge | A61N 1/18 |
| 2017/0224980 A1* | 8/2017 | Grasso | A61N 1/36036 |

FOREIGN PATENT DOCUMENTS

| | | |
|---|---|---|
| WO | 2017091705 A1 | 6/2017 |
| WO | 2017120023 A1 | 7/2017 |
| WO | 2018227088 A1 | 12/2018 |

OTHER PUBLICATIONS

U.S. Appl. No. 16/618,101, filed Nov. 27, 2019, Tyler.
U.S. Appl. No. 16/779,442, filed Jan. 31, 2020, Tyler.
Author Unknown, "NERVANA User Guide," available as early as Jul. 17, 2017, Nervana, LLC, 36 pages.
Author Unknown, "NEMOS Brochure," available as early as Jul. 17, 2017, cerbomed GmbH, 20 pages.
Author Unknown, "How gammaCore Works," available as early as Jul. 17, 2017, electroCore, LLC, 2 pages.

* cited by examiner

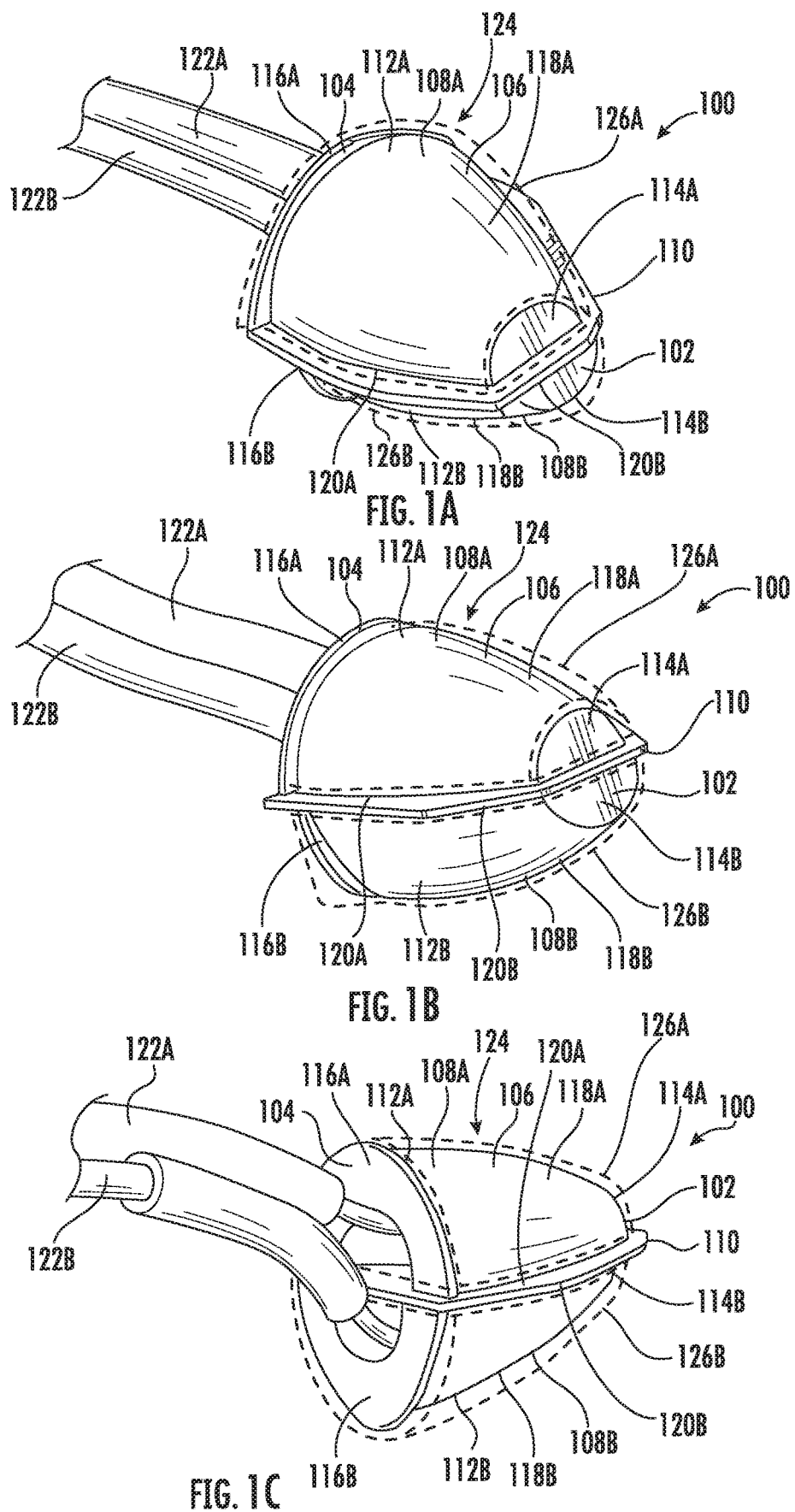

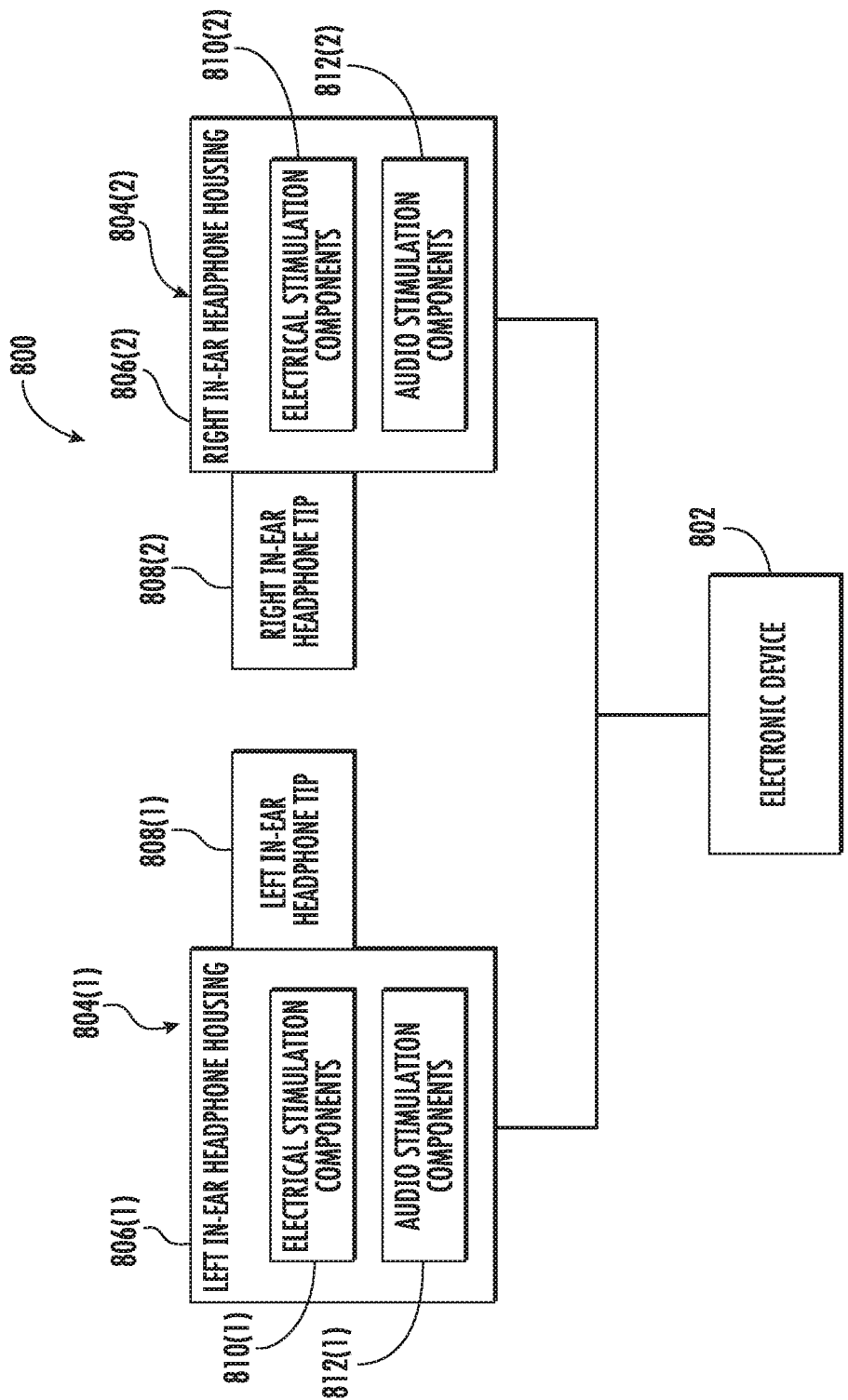

IN-EAR ELECTRODE ASSEMBLY FOR NON-INVASIVE VAGUS NERVE STIMULATION

RELATED APPLICATIONS

This application is a 35 U.S.C. § 371 national phase filing of International Application No. PCT/US18/49157 filed Aug. 31, 2018, and claims priority to U.S. Provisional Patent Application No. 62/552,764 filed Aug. 31, 2017 and U.S. Provisional Patent Application No. 62/633,692 filed Feb. 22, 2018, wherein the entire contents of the foregoing applications are hereby incorporated by reference herein.

TECHNICAL FIELD

The present disclosure relates to non-invasive vagus nerve stimulation. In particular, the present disclosure relates to an in-ear electrode assembly for non-invasive vagus nerve stimulation.

BACKGROUND

Stress and anxiety are common emotional responses with differing levels of severity. In fact, over 40 million people in the U.S. are currently diagnosed with some form of anxiety disorder. There are many things that cause stress and anxiety, but the effects can seriously inhibit one's performance and drive, whether in the workplace, at school, at a public event, playing sports, social environments, etc. Some of the most significant effects include increased perspiration, elevated heart and breathing rate, high blood pressure, muscle tremors, and a list of others. It is not typically the stress itself that causes people to perform poorly, but rather these side effects of stress.

There are various methods to help reduce the effects of stress, but each is limited. Meditation and mindfulness are very popular and natural stress relief methods, but they take large amounts of time and discipline to perform, and the concept is difficult for many people to understand. Recreational drugs and alcohol can immediately help reduce the effects of stress, but they are not considered viable long term treatments and they come with potentially harmful side effects. Other prescription drugs like beta blockers can lower heart rate without any euphoric sensations, but they are expensive, have various side effects, and take a large amount of time before the drug starts to work. People who suffer from stress and anxiety need a solution that is inexpensive and drug-free with immediate relief and little or no side effects.

Vagus Nerve Stimulation (VNS) helps reduce the effects of stress and anxiety and provides treatment for a list of other ailments (e.g., epilepsy). The vagus nerve (cranial nerve X) is part of the autonomic nervous system. It travels from the brain to the neck, chest, and heart where it regulates a list of automatic physiological functions (e.g., parasympathetic response of the heart, lungs, digestive tract, etc.). When it is depolarized (e.g., electrically stimulated), it simultaneously activates the parasympathetic response and deactivates the sympathetic response, resulting in a decreased heart rate and blood pressure. The vagus nerve can be directly stimulated via a pacemaker-like device with electrodes implanted in the neck. However, due to high cost and high risk procedures, invasive methods to stimulate the vagus nerve are not ideal for general stress and anxiety relief.

Alternatively, the vagus nerve can be non-invasively stimulated with electrodes placed in the ear canal or on the surface of the neck, but current methods of stimulating the vagus nerve through the neck or the ear both have limitations that prevent their widespread adoption. In particular, stimulation through the neck typically utilizes a sticky electrode, which requires a user's skin to be prepared with alcohol before each use and requires the user to remain still to prevent the electrode from falling off. Another way to stimulate through the neck is with a handheld device, which can be more comfortable, but inhibits the user's freedom and mobility, since the handheld device must be held against the user's neck for the duration of treatment.

Stimulating the vagus nerve through the ear is generally more appealing than through the neck, but it has its limitations as well. For example, some devices for stimulating the vagus nerve through the ear include electrodes that need to be soaked in a saline solution to work, which may cause the electrodes to be uncomfortable, easily dislodged, and require resoaking after each use (since the saline solution dries quickly). Other ear electrodes can stimulate the vagus nerve without requiring saline solution, but they are neither comfortable nor designed for recreational use by people with active lifestyles. For example, some ear electrodes include spherical metal tips to deliver current to the vagus nerve, but the stimulation is painful due to the low resistance and high current density of the metal electrodes.

These and other technical challenges impede widespread adoption by the public of non-invasive vagus nerve stimulation.

SUMMARY

Disclosed herein are an electrode assembly, an in-ear headphone, an in-ear headphone pair, and an electrode pair assembly, each for non-invasive vagus nerve stimulation. Each of the foregoing items includes a first electrode and a second electrode, which may be fabricated of conductive silicone (e.g., entailing less pain than metal electrodes). An electrode assembly configured for insertion into an ear of a user includes a first electrode, a second electrode, and a shim positioned therebetween to separate and electrically insulate the first electrode and second electrode from one another. In such an electrode assembly, the first electrode and the second electrode may be complementary in shape such that the electrode assembly forms a frustoconical-shape to maximize surface area contact of the electrode assembly within the ear. An in-ear headphone or headphone pair may include an electrode assembly as previously described, in conjunction with a housing and a waveform generator positioned in the housing and configured to apply an electric signal to the electrode assembly. As an alternative to an electrode assembly, an electrode pair assembly may include a first electrode configured for insertion into a first ear of a user, and a second electrode configured for insertion into a second ear of the user, with the electrode pair assembly being configured to form an electrical circuit when the first electrode is positioned in the first ear and the second electrode is positioned in the second ear of the user. Certain embodiments further include audio components positioned within a housing of at least one in-ear headphone to deliver audio stimulation through a central channel of a first electrode or second electrode, respectively.

In some embodiments, an electrode assembly includes an electrically conductive gel with separate portions positioned over the first electrode and/or second electrode (e.g., a first conductive gel portion on the first electrode and a second conductive gel portion on the second electrode) to increase distribution of current density for a more pleasant user experience without requiring reapplication between uses. For example, the conductive gel may include a hydrogel (e.g., dry and/or firm, etc.) deposited (e.g., pre-applied) on the first electrode and the second electrode, such as during a manufacturing process. In this way, the hydrogel stays in place on the first electrode and the second electrode and application by a consumer is not required. In some embodiments, the electrode assembly may be formed into an in-ear headphone tip, such as used in an in-ear headphone pair, to provide both electrical stimulation and audio stimulation to the ear. Accordingly, the dry and reusable electrode assembly maximizes or at least enhances skin contact for better non-invasive stimulation of the vagus nerve and increases current distribution for a more pleasant user experience.

In an aspect, the present disclosure relates to an electrode assembly for non-invasive nerve stimulation comprising a first electrode, a second electrode, and a shim. The first electrode forms a first body portion. The second electrode forms a second body portion complementary to the first body portion such that the first body portion of the first electrode and the second body portion of the second electrode in combination form a frustoconical-shape. The shim, optionally formed of a plastic material, is positioned between the first electrode and the second electrode to separate and electrically insulate the first electrode and the second electrode from each other. The electrode assembly is configured for insertion into an ear of a user of the electrode assembly to form an electrical circuit including the first electrode, the second electrode, and a vagus nerve of the user to electrically stimulate the vagus nerve.

In certain embodiments, the first electrode and the second electrode comprise conductive silicone. In certain embodiments, the shim comprises a plastic material. In certain embodiments, the electrode assembly further comprises a conductive gel covering at least a portion of an outer surface of at least one of the first electrode or the second electrode. In certain embodiments, the conductive gel comprises a hydrogel.

In certain embodiments, the shim comprises a ridge that extends beyond the outer surface of the first electrode and the second electrode. The conductive gel comprises a first gel portion covering at least a portion of the first electrode and a second gel portion covering at least a portion of the second electrode. The first gel portion and the second gel portion are electrically insulated from each other by the ridge. In certain embodiments, the first electrode and the second electrode are substantially a same size and the shim is positioned in an approximate middle of the electrode assembly. In certain embodiments, the first electrode and the second electrode are differently sized and the shim is positioned offset from a middle of the electrode assembly.

In another aspect, the present disclosure relates to an in-ear headphone comprising a housing, an electrode assembly, and a waveform generator. The electrode assembly forms an in-ear headphone tip attached to the housing. The electrode assembly comprises a first electrode, a second electrode, and a shim. The first electrode forms a first body portion. The second electrode forms a second body portion complementary to the first body portion such that the first body portion of the first electrode and the second body portion of the second electrode in combination form a frustoconical-shape. The shim is positioned between the first electrode and the second electrode to separate and electrically insulate the first electrode and the second electrode from each other. The electrode assembly is configured for insertion into an ear of a user to form an electrical circuit including the first electrode, the second electrode, and a vagus nerve of the user to electrically stimulate the vagus nerve. The waveform generator is positioned within the housing and configured to apply an electric signal to the electrode assembly to stimulate the vagus nerve.

In certain embodiments, the first electrode and the second electrode comprise conductive silicone. In certain embodiments, the shim comprises a plastic material. In certain embodiments, the in-ear headphone further comprises a conductive gel covering at least a portion of an outer surface of at least one of the first electrode or the second electrode. In certain embodiments, the in-ear headphone comprises a signal transmitter and a signal receiver configured to permit wireless communication with an electronic device external to the in-ear headphone. In certain embodiments, the in-ear headphone is configured to allow a user to adjust an operating parameter of the waveform generator by an electronic device. The operating parameter comprises at least one of intensity, duration, or pulse pattern. In certain embodiments, the in-ear headphone comprises audio components within the housing. The audio components are configured to deliver audio stimulation through a central channel defined in the electrode assembly. The in-ear headphone is configured to provide the audio stimulation concurrently with electrical stimulation of the vagus nerve.

In another aspect, the present disclosure relates to an in-ear headphone pair comprising a right in-ear headphone and a left in-ear headphone. The right in-ear headphone is configured for insertion into a right ear, and comprises audio components configured to deliver audio stimulation to the right ear. The left in-ear headphone is configured for insertion into a left ear, and comprises a housing, an electrode assembly, a waveform generator, and audio components. The electrode assembly forms an in-ear headphone tip attached to the housing. The electrode assembly comprises a first electrode, a second electrode, and a shim. The first electrode forms a first body portion. The second electrode forms a second body portion complementary to the first body portion such that the first body portion of the first electrode and the second body portion of the second electrode in combination form a frustoconical-shape. The shim is positioned between the first electrode and the second electrode to separate and electrically insulate the first electrode and the second electrode from each other. The electrode assembly is configured for insertion into an ear of a user to form an electrical circuit including the first electrode, the second electrode, and a vagus nerve of the user of the electrode assembly to electrically stimulate the vagus nerve. The waveform generator is positioned within the housing and configured to apply an electrical signal to the electrode assembly to stimulate the vagus nerve. The audio components are positioned within the housing and configured to deliver audio stimulation to the left ear through a central channel of the electrode assembly.

In certain embodiments, the first electrode and the second electrode comprise conductive silicone. In certain embodiments, the shim comprises a plastic material. In certain embodiments, the in-ear headphone pair further comprises a conductive gel covering at least a portion of an outer surface of at least one of the first electrode or the second electrode. In certain embodiments, the in-ear headphone comprises a signal transmitter and a signal receiver configured to permit wireless communication with an electronic device external to the in-ear headphone pair. In certain embodiments, the left in-ear headphone is configured to deliver the audio stimulation concurrently with electrical stimulation.

In another aspect, the present disclosure relates to an electrode pair assembly for non-invasive nerve stimulation comprising a first electrode and a second electrode. The first electrode forms a first frustoconical-shape configured for insertion into a first ear of a user, and the second electrode forms a second frustoconical-shape configured for insertion into a second ear of the user. The electrode pair assembly is configured to form an electrical circuit when the first electrode is positioned within the first ear of the user and the second electrode is positioned within the second ear of the user. The electrical circuit includes the first electrode, the second electrode, and a vagus nerve of the user to electrically stimulate the vagus nerve.

In certain embodiments, the first electrode and the second electrode are in conductive electrical communication via electrical wiring. In certain embodiments, at least one of the first electrode or the second electrode comprises conductive silicone. In certain embodiments, at least one of the first electrode or the second electrode comprises a conductive gel. In certain embodiments, the electrode pair assembly further comprises a conductive gel covering at least a portion of an outer surface of at least one of the first electrode or the second electrode. In certain embodiments, the conductive gel comprises a hydrogel. In certain embodiments, the first electrode comprises a first conductive gel forming the first frustoconical-shape, and the second electrode comprises a second conductive gel forming the second frustoconical-shape. In certain embodiments, the first conductive gel comprises a first hydrogel and the second conductive gel comprises a second hydrogel.

In another aspect, the present disclosure relates to an in-ear headphone pair comprising a first in-hear headphone and a second in-ear headphone. The first in-ear headphone is configured for insertion into a first ear of a user. The first in-ear headphone comprises a first housing, a first electrode, and first audio components. The first electrode forms a first in-ear headphone tip attached to the first housing. The first electrode defines a first central channel. The first audio components are positioned within the first housing and are configured to deliver audio stimulation to the first ear through the first central channel of the first electrode. The second in-ear headphone is configured for insertion into a second ear of the user. The second in-ear headphone comprises a second housing, a second electrode, and second audio components. The second electrode forms a second in-ear headphone tip attached to the second housing. The second electrode defines a second central channel. The second audio components are positioned within the second housing and are configured to deliver audio stimulation to the second ear through the second central channel of the second electrode. The in-ear headphone pair is configured to form an electrical circuit when the first electrode is positioned within the first ear of the user and the second electrode is positioned within the second ear of the user. The electrical circuit includes the first electrode, the second electrode, and a vagus nerve of the user to electrically stimulate the vagus nerve.

In certain embodiments, the in-ear headphone pair further comprises electrical wiring electrically connecting the first electrode to the second electrode. In certain embodiments, at least one of the first electrode or the second electrode comprises conductive silicone. In certain embodiments, at least one of the first electrode or the second electrode comprises an electrically conductive gel. In certain embodiments, the in-ear headphone pair further comprises a conductive gel covering at least a portion of an outer surface of at least one of the first electrode or the second electrode. In certain embodiments, the conductive gel comprises a hydrogel. In certain embodiments, the first electrode forms a first frustoconical-shape and the second electrode forms a second frustoconical-shape. In certain embodiments, the first electrode comprises a first conductive gel forming the first frustoconical-shape, and the second electrode comprises a second conductive gel forming the second frustoconical-shape. In certain embodiments, the first conductive gel comprises a first hydrogel and the second conductive gel comprises a second hydrogel. In certain embodiments, at least one of the first in-ear headphone or the second in-ear headphone comprises a signal transmitter and a signal receiver configured to permit wireless communication with an electronic device external to the first in-ear headphone and the second in-ear headphone. In certain embodiments, at least one of the first in-ear headphone or the second in-ear headphone is configured to deliver the audio stimulation concurrently with electrical stimulation. In certain embodiments, at least one of the first in-ear headphone or the second in-ear headphone includes a waveform generator configured to apply an electrical signal to at least one of the first electrode or the second electrode. In certain embodiments, the at least one of the first in-ear headphone and the second in-ear headphone is configured to allow the user to adjust an operating parameter of the waveform generator by an electronic device. The operating parameter comprises at least one of intensity, duration, or pulse pattern. In certain embodiments, the waveform generator is configured to deliver a biphasic waveform.

In certain embodiments, one of the first electrode or the second electrode comprises an anode, and the other of the first electrode or the second electrode comprises a cathode.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the preferred embodiments in association with the accompanying drawing figures.

BRIEF DESCRIPTION OF DRAWINGS

FIG. 1A is a top front perspective view of an electrode assembly for non-invasive vagus nerve stimulation with wires attached thereto;

FIG. 1B is another top front perspective view of the electrode assembly of FIG. 1A;

FIG. 1C is a top back perspective view of the electrode assembly of FIG. 1A;

FIG. 8 is a general diagram illustrating the in-ear headphone pair of FIG. 7.

DETAILED DESCRIPTION

Figure 2A:
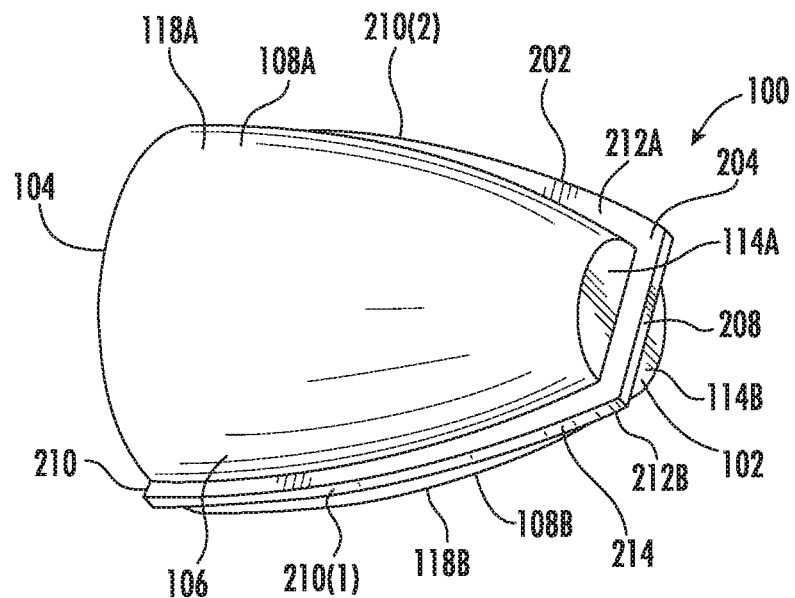
FIG. 2A is a top front perspective view of the electrode assembly of FIGS. 1A-1C with a shim with ridges for separating a first electrode and a second electrode, and separating portions of conductive gel on each of the first electrode and the second electrode.
Figure 2B:
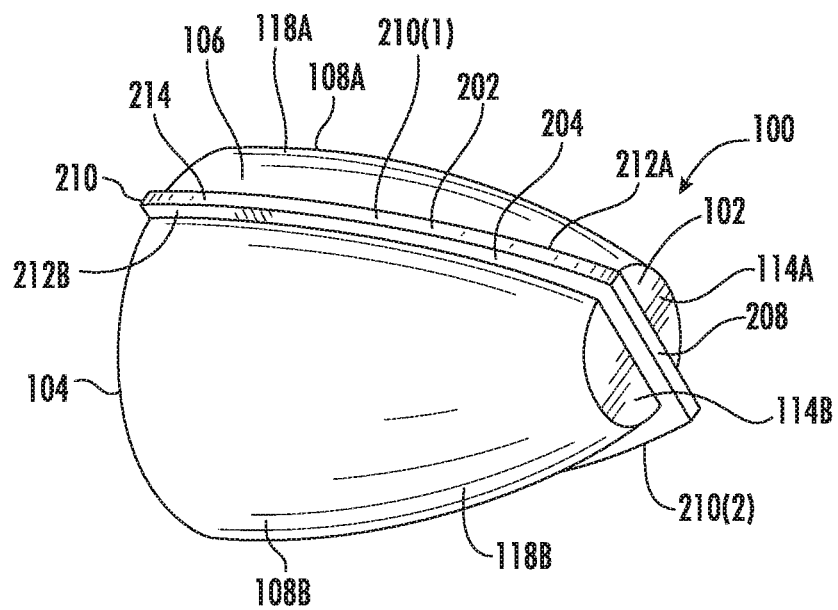
FIG. 2B is a bottom perspective view of the electrode assembly of FIG. 2A.
Figure 2C:
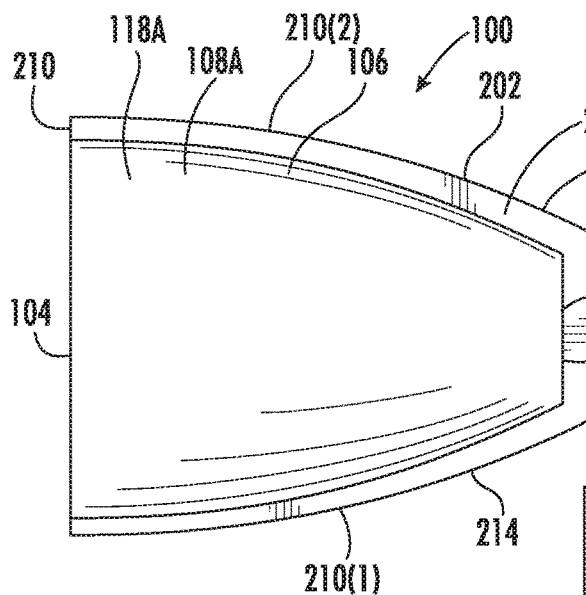
FIG. 2C is a top elevation view of the electrode assembly of FIG. 2A.
Figure 2D:
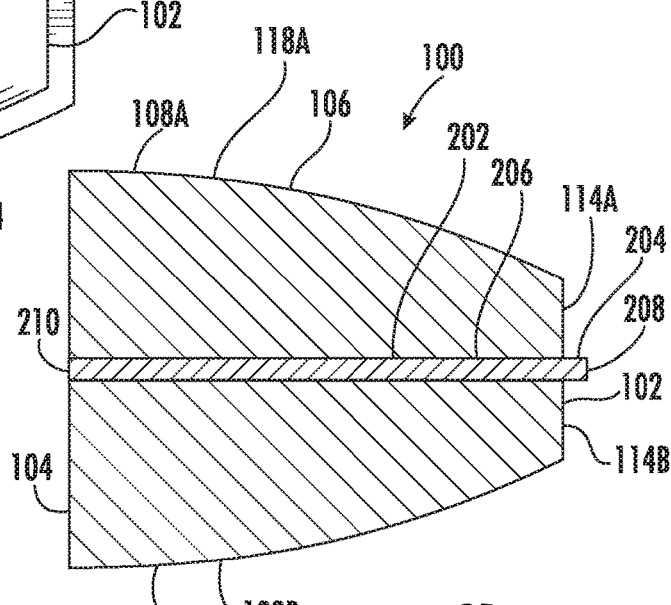
FIG. 2D is a cross-sectional side view of the electrode assembly of FIG. 2A.
Figure 2E:
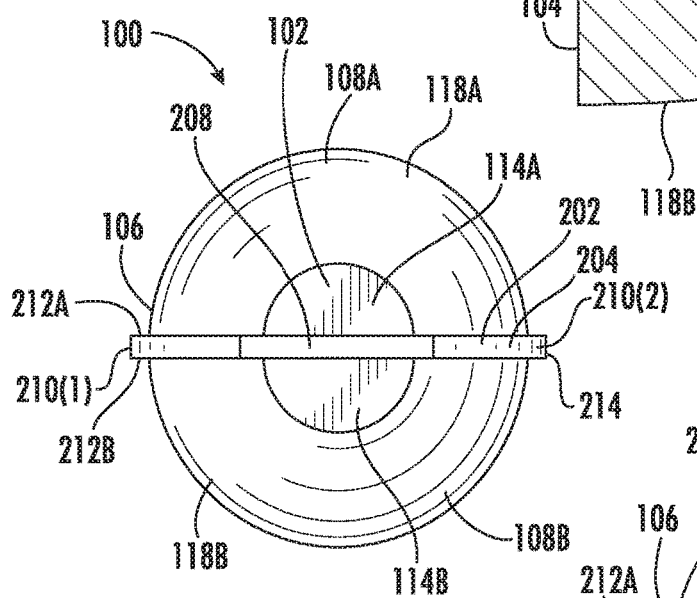
FIG. 2E is a front elevation view of the electrode assembly of FIG. 2A.
Figure 2F:
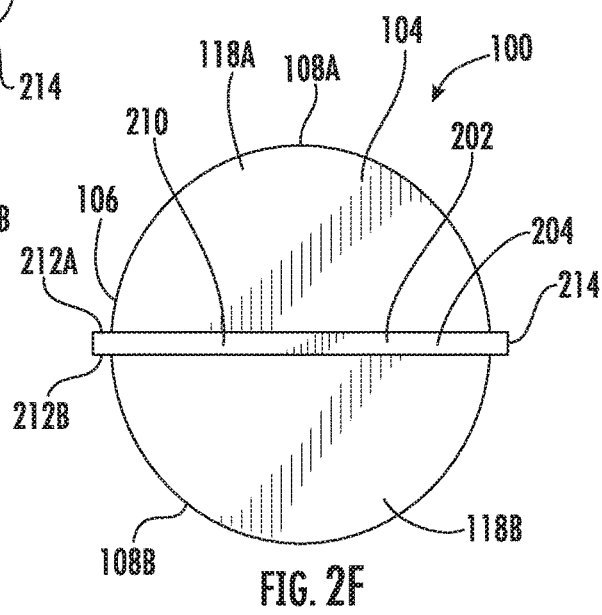
FIG. 2F is a back elevation view of the electrode assembly of FIG. 2A.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the drawing figures. It will be understood that these terms and those discussed above are intended to encompass different orientations of the device in addition to the orientation depicted in the drawing figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Disclosed herein is an electrode assembly for non-invasive vagus nerve stimulation. In particular, the electrode assembly is configured for insertion into an ear of a user and includes a first electrode, a second electrode, and a shim positioned therebetween. The first electrode and second electrode may be made of conductive silicone which provides for improved stimulation (e.g., less painful than metal electrodes). The shim separates and electrically insulates the first electrode from the second electrode from each other. The first electrode and the second electrode are complementary in shape such that the electrode assembly forms a frustoconical-shape to maximize surface area contact of the electrode assembly within the ear. In some embodiments, the electrode assembly includes a conductive gel with separate portions positioned over the first electrode and/or second electrode (e.g., a first conductive gel portion on the first electrode and a second conductive gel portion on the second electrode) to increase distribution of current density for a more pleasant user experience and which does not need to be reapplied between uses. For example, the conductive gel may include a hydrogel (e.g., dry and/or firm, etc.) deposited (e.g., pre-applied) on the first electrode and the second electrode, such as during a manufacturing process. In this way, the hydrogel stays in place on the first electrode and the second electrode and post-sale application by a consumer is not required. In some embodiments, the electrode assembly may be formed into an in-ear headphone tip, such as used in an in-ear headphone pair, to provide both electrical stimulation and audio stimulation to the ear. Accordingly, the dry and reusable electrode assembly maximizes skin contact for better non-invasive stimulation of the vagus nerve and increases current distribution for a more pleasant user experience.

FIGS. 1A-1C are views of an electrode assembly 100 for non-invasive vagus nerve stimulation. In particular, the electrode assembly 100 is configured for non-invasively stimulating (e.g., modulating) the activity of one or more nerve parts of the auricular branch of the vagus nerve. Stimulating (e.g., depolarizing) the vagus nerve can have significant relaxing effects on the body, such as by lowering heart rate and blood pressure, reducing breathing rate and adrenaline, etc. Accordingly, devices disclosed herein may be used for medical or therapeutic purposes, mitigating deleterious side effects of high stress jobs or situations, etc.

The electrode assembly 100 is configured for insertion into an ear canal of an ear of a user. The electrode assembly 100 is of a generally frustoconical-shape, which as used herein, includes shapes generally similar to a cone, parabolic cone, elliptical cone, etc. In other words, the frustoconical-shape, as used herein, refers to a truncated bell-shape, flat-nose bullet-shape, truncated ellipsoidal cone, truncated parabolic cone, etc. In particular, the electrode assembly 100 includes a proximal end 102 (e.g., planar proximal end), a distal end 104 (e.g., planar distal end) opposite the planar proximal end 102, and a curved outer surface 106. However, other shapes could be used, such as a semi-spherical shape, etc.

The electrode assembly 100 includes a first electrode 108A (e.g., anode), a second electrode 108B (e.g., cathode), and a shim 110 positioned therebetween. In other words, the electrode assembly 100 includes an electrode pair including the first electrode 108A and the second electrode 108B. One or both of the first electrode 108A and the second electrode 108B include a conductive material, such as conductive silver and/or conductive silicone (e.g., carbon filled silicone, silver filled silicone, etc.). The first electrode 108A and the second electrode 108B are complementary in shape to form the overall frustoconical-shape of the electrode assembly 100. In particular, the first electrode 108A includes a first body portion 112A having a proximal end 114A, a distal end 116A opposite the proximal end 114A, a curved outer surface 118A extending between the proximal end 114A and distal ends 116A, and a planar internal surface 120A extending between the proximal end 114A and the distal end 116A. Similarly, the second electrode 108B includes a second body portion 112B having a proximal end 114B, a distal end 116B opposite the proximal end 114B, a curved outer surface 118B extending between the proximal end 114B and the distal end 116B, and a planar internal surface 120B extending between the proximal end 114B and the distal end 116B. Accordingly, when assembled, the internal surfaces 120A, 120B of the first electrode 108A and the second electrode 108B are proximate to one another, such that the proximal ends 114A, 114B, distal ends 116A, 116B, and curved outer surfaces 118A, 118B of the first electrode 108A and the second electrode 108B form the overall frustoconical-shape of the electrode assembly 100. In other words, the first body portion 112A of the first electrode 108A and the second body portion 112B of the second electrode 108B in combination form the frustoconical-shape of the electrode assembly 100. Further, the electrode assembly 100 includes a first wire 122A connected to the distal end 116A of the first electrode 108A and a second wire 122B connected to the distal end 116B of the second electrode 108B. The first and the second wires 122A, 122B may be inserted into the first electrode 108A and the second electrode 108B (e.g., pressed into during or after the curing phase of the anode 108A and second electrode 108B) or otherwise touching the first electrode 108A and the second electrode 108B. For example, rather than inserting the wires 122A, 122B into the first electrode 108A and the second electrode 108B, the electrode assembly 100 (e.g., first electrode 108A and the second electrode 108B) may be configured with one or more holes (as similarly shown in FIGS. 4A-4F) to slide over and contact at least a portion of a first wire 122A and the second wire 122B, such as where the first wire 122A and the second wire 122B are exposed metal contacts of an in-ear housing. Such a configuration may make the manufacturing process less complex and allow for an improved user experience.

The frustoconical-shape of the electrode assembly 100 facilitates insertion into user ears of various sizes and increases the surface area of contact between the electrode assembly 100 and skin (e.g., skin tissue) within the ear canal of the ear of the user. Further, it is noted that the electrode assembly 100 is configured to be inserted such that the shim 110 is oriented horizontally to a head of the user. In other words, the electrode assembly 100 is configured for insertion such that the shim 110 extends from front to back of the head of the user (not vertically from top to bottom). Such an orientation provides electrical stimulation within the ear canal from top to bottom (not front to back). In particular, in certain embodiments, the first electrode 108A includes the anode and the second electrode 108B includes the cathode such that electrical stimulation within the ear canal is from top to bottom. This increases the effectiveness of stimulating the vagus nerve, since nerve endings of the vagus nerve are more concentrated in the bottom of the ear canal.

The shim 110 is positioned between the first electrode 108A and the second electrode 108B to separate and electrically insulate the first electrode 108A and the second electrode 108B from each other. In this way, when the electrode assembly 100 is positioned within the ear, the skin (e.g., skin tissue) within the ear canal of the user completes the circuit. The shim 110 may be made of plastic or other electrically insulative material and may be of any thickness (e.g., 0.5 mm, 1 mm, 2 mm, etc.). The shim 110 is shown as planar, but in other embodiments may be angled in a non-planar configuration, as explained below in more detail. The shim 110 is positioned in the general middle of the electrode assembly 100 to bisect the first electrode 108A and the second electrode 108B. In other words, the shim 110 intersects and is oriented along a center axis of the electrode assembly 100. In particular, the shim 110 is positioned proximate the planar surfaces 120A, 120B of the first electrode 108A and the second electrode 108B and extends from the proximal end 102 and distal end 104 of the electrode assembly 100 and from one side of the curved outer surface through a center of the electrode assembly to another side of the curved outer surface. In this way, the first electrode 108A and the second electrode 108B are about the same size (e.g., same volume, same dimensions, etc.).

When the electrode assembly 100 is inserted into an ear of a user and an electrical signal is generated, an electrical circuit is formed which includes the first electrode 108A, second electrode 108B, skin tissue within the ear canal of the user, and vagus nerve of the user to electrically stimulate the vagus nerve. The electrical signal could be alternating current (AC) or direct current (DC). In certain embodiments, the electrical signal comprises a pulsed DC signal.

As explained in more detail below, an electrically conductive gel 124 (e.g., a hydrogel) may be applied to the curved outer surface 106 of the electrode assembly 100 to maximize contact with the skin in the ear canal and to increase current distribution for increased comfort. For illustrative purposes, the conductive gel 124 is shown in dashed lines. In other words, it reduces a sensation of electric shock experienced by the user. When applied, the conductive gel 124 (also referred to herein as a conductive gel coating, etc.) includes a first portion 126A in contact with and/or covering the first electrode 108A, and a second portion 126B in contact with and/or covering the second electrode 108B. The conductive gel 124 increases distribution of current density within the ear canal for increased comfort during stimulation for a better user experience. Further, the conductive gel 124 does not need to be reapplied between uses, since it does not wear off easily and does not dry out quickly, especially compared with saline. Additionally, the friction and feel of the conductive gel 124 is improved, and is also less likely to fall out since it is more viscous than saline. Accordingly, the electrode assembly 100 provides reusable, comfortable, and drier stimulation of the vagus nerve.

FIGS. 2A-2F are views of another embodiment of the electrode assembly 200 of FIGS. 1A-1C with a shim 110 with ridges 204. The shim 110 includes an internal planar surface 206 (see FIG. 2D) positioned between the first electrode 108A and the second electrode 108B and a ridge 204 extending from an outer surface 106 of the electrode assembly 100. The ridge 204 includes a proximal end 208 extending past the proximal ends 114A, 114B of the first electrode 108A and the second electrode 108B, and first and second curves 210(1), 210(2) extending past the curved outer surfaces 118A, 118B of the first electrode 108A and the second electrode 108B. These ridges 204 further ensure electrical insulation between the first electrode 108A and the second electrode 108B. Further, the ridges 204 provide an attachment point and divide for the first and second portions 126A, 126B of the conductive gel 124 (see FIGS. 1A-1C). In particular, the first portion 126A of the conductive gel 124 may be attached to the first electrode 108A by an adhesive (e.g., glue). The adhesive may be positioned on the curved outer surface 118A of the first electrode 108A, the proximal end 114A of the first electrode 108A, and/or a portion of a first surface 212A of the ridge 204 of the shim 110. Similarly, the second portion 126B of the conductive gel 124 may be attached to the second electrode 108B by an adhesive (e.g., glue). The adhesive may be positioned on the curved outer surface 118B of the second electrode 108B, the proximal end 114B of the second electrode 108B, and/or a portion of a second surface 212B of the ridge 204 of the shim 110. Alternatively, in other embodiments, the conductive gel 124 is a hydrogel and may be placed on the first electrode 108A and/or the second electrode 108B by hydrogel deposition techniques without the use of an adhesive. In this way, the ridges 204 of the shim 110 electrically insulate the first and second hydrogel portions 126A, 126B from each other (see FIGS. 1A-1C). The height of each ridge 204 may be configured to be the same thickness as, or to have a greater thickness than, the thickness of the conductive gel 124. In this way, after the conductive gel 124 is applied to the electrode assembly 100, the conductive gel 124 may be approximately flush with the edge surface 214 of the ridge 204. It is noted that the shim 110 may instead be flush with the proximal end 102, distal end 104, and/or curved outer surface 106 of the electrode assembly 200, as discussed in more detail below.

In other embodiments, the conductive gel 124 may be attached to the first electrode 108A and second electrode 108B by dipping the assembled first electrode 108A and second electrode 108B in uncured hydrogel, and then cutting the hydrogel along the shim 110 to separate the first and second portions 126A, 126B of the conductive gel 124.

Figure 3:
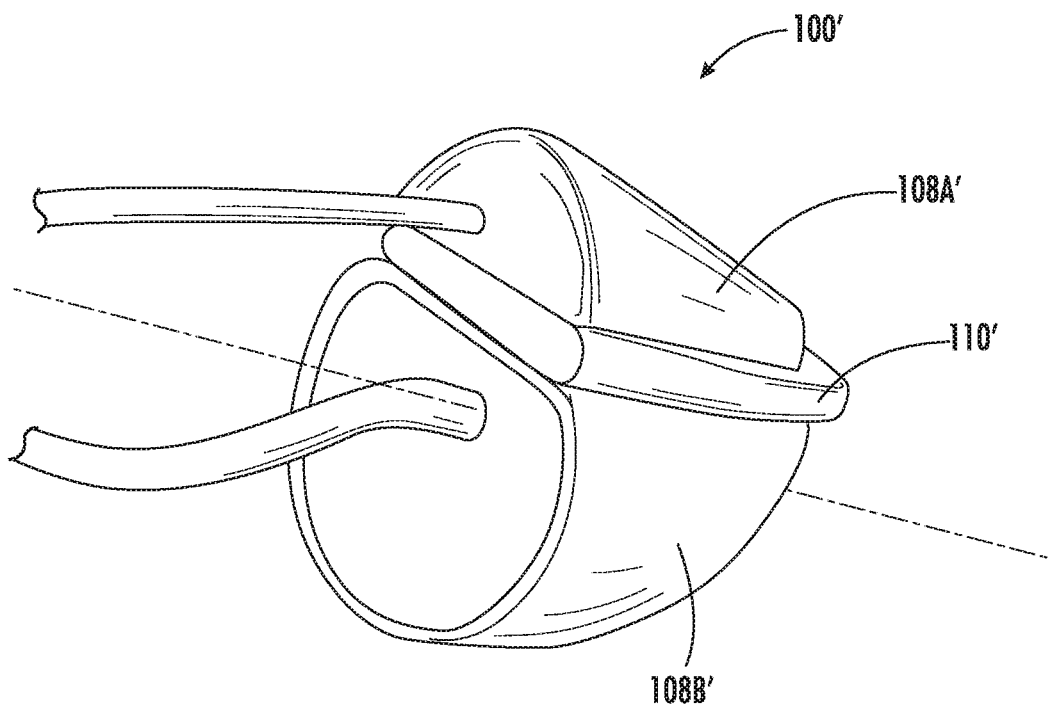
FIG. 3 is a perspective view of another embodiment of the electrode assembly of FIGS. 1A-2F with an offset shim separating an asymmetric first electrode and second electrode.
Figure 4A:
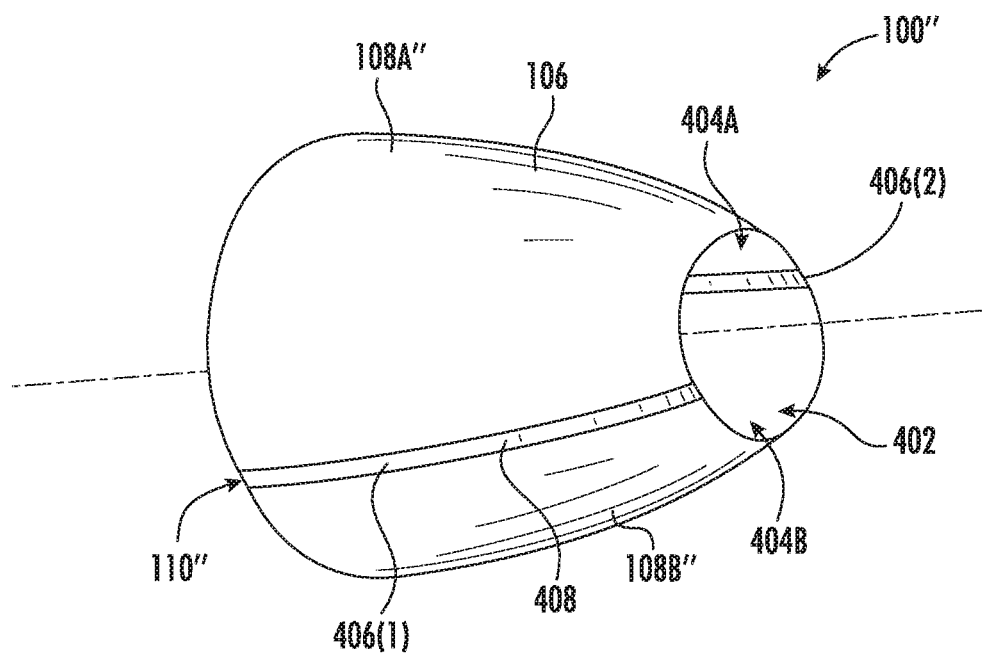
FIG. 4A is a top front perspective view of another embodiment of the electrode assembly of FIGS. 1A-2F forming an in-ear headphone tip.
Figure 4B:
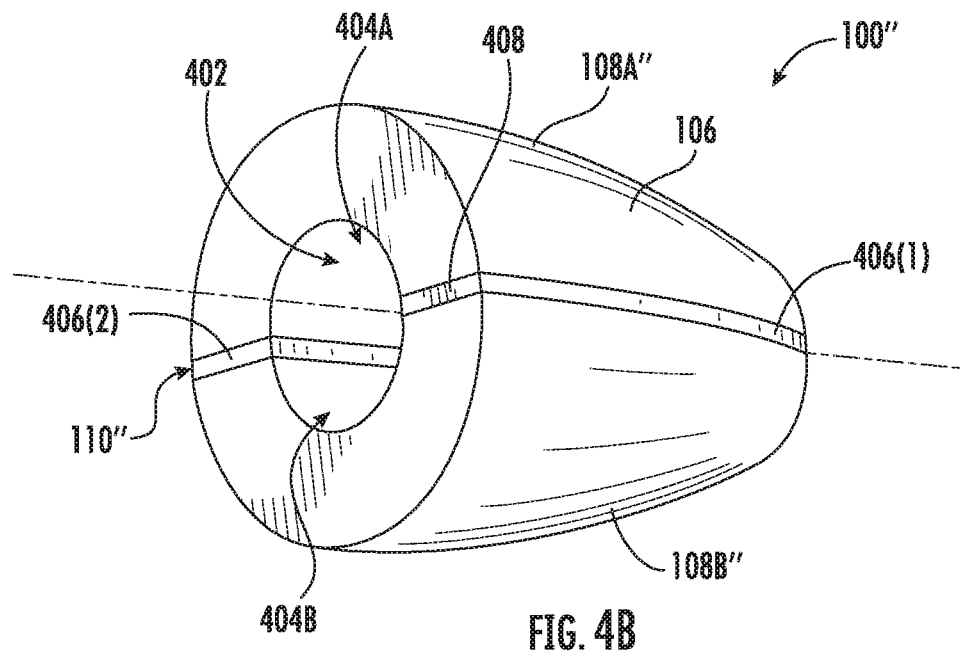
FIG. 4B is a bottom perspective view of the electrode assembly of FIG. 4A.
Figure 4C:
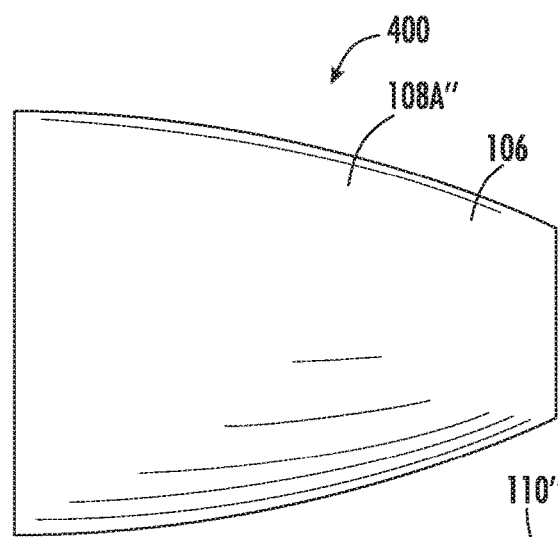
FIG. 4C is a top elevation view of the electrode assembly of FIG. 4A.
Figure 4D:
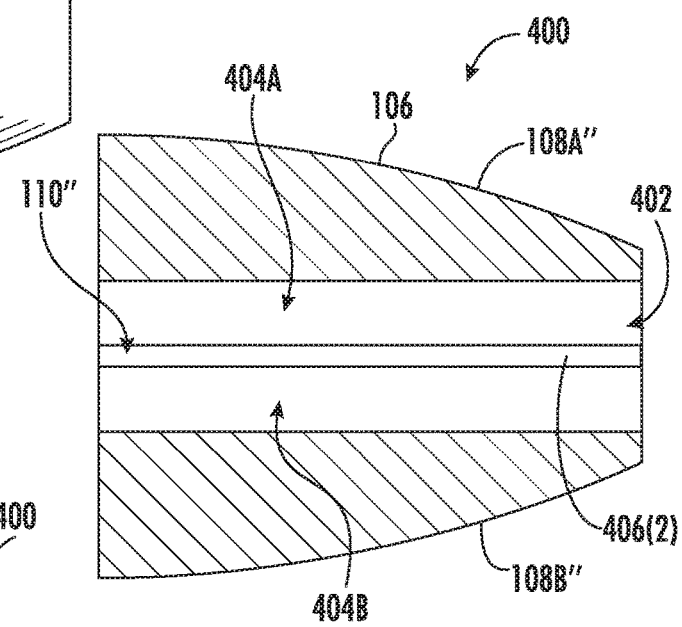
FIG. 4D is a cross-sectional side view of the electrode assembly of FIG. 4A.
Figure 4E:
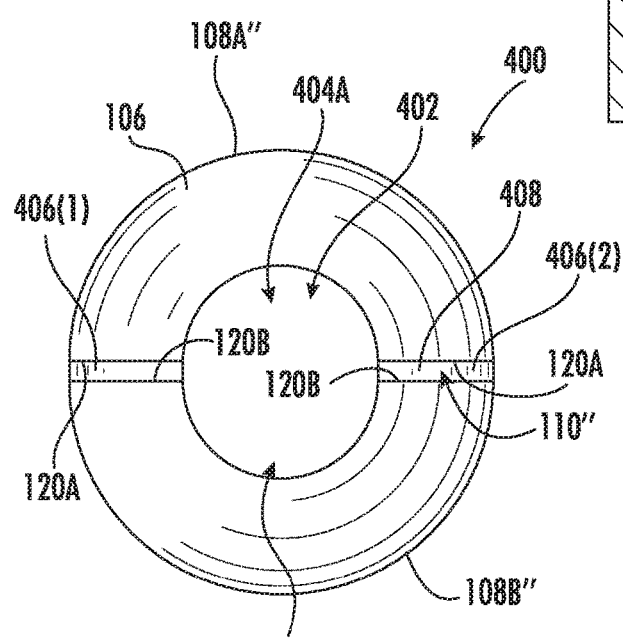
FIG. 4E is a front elevation view of the electrode assembly of FIG. 4A.
Figure 4F:
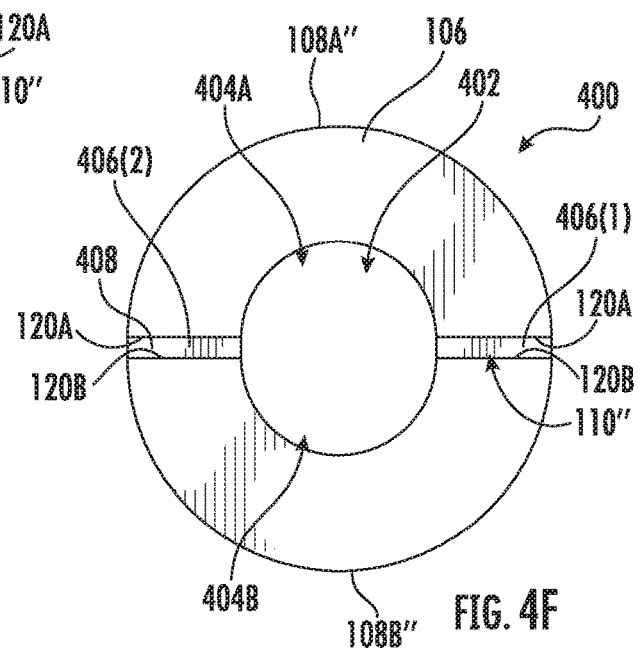
FIG. 4F is a back elevation view of the electrode assembly of FIG. 4A.

FIG. 3 is a perspective view of another embodiment of the electrode assembly 100 of FIGS. 1A-2F with an offset shim 110. The shim 110' of FIG. 3 is offset from a center of the electrode assembly 100' such that the first electrode 108A' is smaller than the second electrode 1086'. In other words, the shim 110' extends parallel and offset to a central axis of the electrode assembly. In such a configuration, the volume and surface area of the first electrode 108A' are smaller than the volume and surface area, respectively, of the second electrode 1086'. Accordingly, in such a configuration, the electrode assembly 100' is configured to be oriented within the ear canal such that the second electrode 108B' (e.g., the cathode) is toward a bottom of the ear canal. Increasing the surface area of contact of the second electrode 108B' (e.g., cathode) increases the contact area of the second electrode 108B' with the bottom of the ear canal and thereby improves electrical stimulation of the vagus nerve. Accordingly, decreasing the size of the first electrode 108A' (e.g., anode) and respective contact area thereof relative to the second electrode 108B' improves performance, however, decreasing the size of the first electrode 108A' too much limits the magnitude of the electrical connection, and correspondingly limits electrical stimulation of the vagus nerve. Thus, the size of the first electrode 108A' should be decreased but not to a degree that would unduly limit the electrical connection.

It is noted that the shim 110' may be offset such that the second electrode 108B' (e.g., cathode) is smaller than the first electrode 108A' (e.g., anode), but that in such a configuration the electrode assembly 100' is configured to be oriented within the ear canal such that the first electrode 108A' (e.g., anode) is toward a bottom of the ear canal. It is also noted that the relative sizes of the first electrode 108A' and the second electrode 108B' may be varied in other ways, such as by using a shim 110' that forms an angle along (i.e., is non-parallel to) the central axis of the electrode assembly 100.

FIGS. 4A-4F are views of another embodiment of the electrode assembly of FIGS. 1A-2F forming an in-ear headphone tip 100". The in-ear headphone tip 100" (may also be referred to herein as an electrode assembly) defines a central channel 402 extending along the central axis of the in-ear headphone tip 100". In particular, the internal surfaces 120A, 120B of the first electrode 108A" and the second electrode 108B" each include a channel portion 404A, 404B extending from the proximal end 114A to the distal end 116B of the first electrode 108A" and the second electrode 108B". As a result, the shim 110" includes first and second segments 406(1), 406(2) separated by the channel 402 therebetween. The channel 402 is configured to attach to or receive a portion of a housing and/or audio speaker of a conventional in-ear headphone, thereby allowing for audio stimulation through the channel simultaneously or concurrently with electrical stimulation.

The shim 110" includes an edge surface 408 flush with the ends 114A, 114B and/or curved outer surface 106 of the in-ear headphone tip 100". It is noted that the shim 110" may include a ridge as discussed above. As with the electrode assembly 100, 100' of FIGS. 1A-3 discussed above, a conductive gel 124 (see FIGS. 1A-1C) may be applied to the outer surface 106 of the first electrode 108A" and the second electrode 108B". Where the edge surface 408 of the shim 110" is flush, the conductive gel 124 may be applied, and then cut to form a gap between the first and second portions 126A, 126B of the conductive gel 124, thereby electrically insulating the first and second portions 126A, 126B of the conductive gel 124.

The in-ear headphone tip 100" has the same form as a conventional in-ear headphone tip seen on a consumer pair of in-ear headphones. In some embodiments, the in-ear headphone 100" is fabricated by pouring the wet silver/silicone rubber into a custom-made mold. As the silver/silicone rubber dries (e.g., over a 24 hours period), the plastic shim 110" is placed down the middle of the silver/silicone rubber. After the shim 110" is placed in the mold, thin wires are inserted into the conductive silicone near the edges. When the in-ear headphone dries (e.g., after 24 hours), it is removed from the mold and dipped into the conductive gel 124.

Another fabrication process includes pouring the conductive silicone into a mold and then curing the conductive silicone (e.g., letting the molded silicone dry). Then the conductive silicone can be cut (e.g., cut in half) to form the first electrode 108" and the second electrode 108B". Conductive gel 124 (e.g., hydrogel) can be applied (e.g., adhered) to each of the first electrode 108" and the second electrode 108B". The first electrode 108" and the second electrode 108B" can then be adhered to opposite sides of the shim 110".

It is noted that the wires can be inserted into the conductive silicone during the curing phase. In another embodiment, the wires protrude outward (or are otherwise exposed) relative to the in-ear housing, and the in-ear headphone can be pressed over the wires (rather than into the wires). In this way, as long as the wires are in insulated contact with each half of the electrode assembly, current is delivered through the whole electrode assembly.

Figure 5:
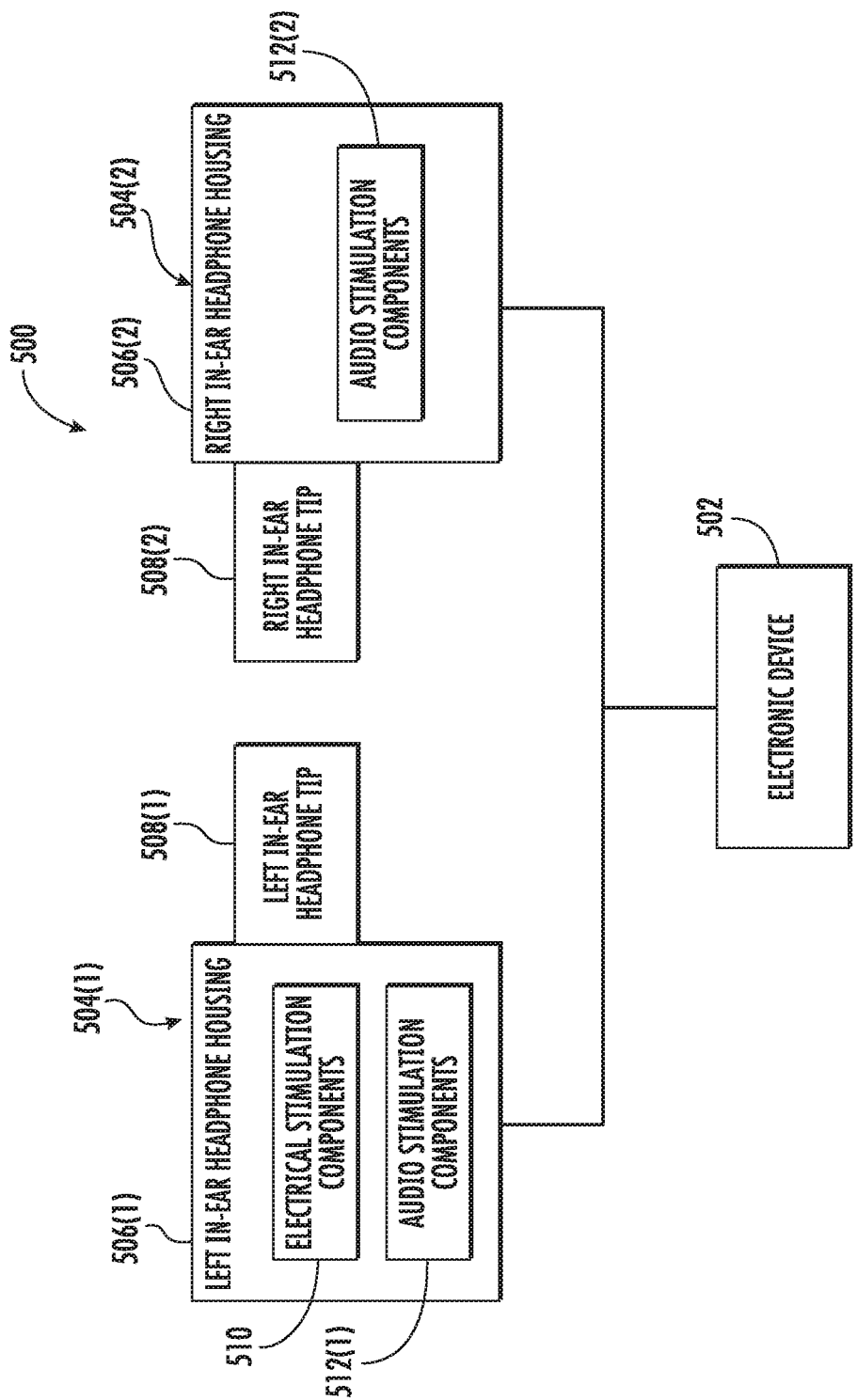
FIG. 5 is a general diagram illustrating an in-ear headphone pair including the in-ear headphone tip of FIGS. 4A-4F.

FIG. 5 is a general diagram illustrating an in-ear headphone pair 500 including the in-ear headphone tip 100" of FIGS. 4A-4F. An in-ear headphone pair 500 includes an electronic device 502, a left in-ear headphone 504(1), and a right in-ear headphone 504(2).

The left in-ear headphone 504(1) includes a housing 506(1) and a left in-ear headphone tip 508(1), as discussed with respect to FIGS. 4A-4F. The left and right in-ear headphones 504(1), 504(2) have the same form as a conventional in-ear headphone seen on a consumer pair of in-ear headphones. The left in-ear headphone housing 506(1) includes electrical stimulation components 510 and audio stimulation components 512(1). The electrical stimulation components 510 include a waveform generator to provide the electrical stimulation parameters. The waveform generator may be configured to deliver a biphasic waveform (e.g., periodically altering the direction of current between the first electrode and the second electrode by periodically flipping polarity). The stimulation waveform parameters can produce an output of 0-20 mA at a frequency of 0-1 MHz and pulse width of 0-1000 us. The audio stimulation components 512(1), 512(2) include a speaker. In particular, it is anticipated that at least a portion of the housing 506(1) may be inserted into the central channel 402 (see FIGS. 4A-4F) of the left in-ear headphone tip 508(1) to attach the housing 506(1) and the left in-ear headphone tip 508(1) to one other.

The right in-ear headphone 504(2) includes a housing 506(2) and a right in-ear headphone tip 508(2) with audio stimulation components 512(2) positioned within the housing 506(2). Only the left in-ear headphone 504(1) includes the electrical stimulation components 510 as the left ear canal contains a higher density of vagal nerve afferents than the right ear canal. However, in certain embodiments, the right in-ear headphone 504(2) may also include electrical stimulation components similar to those of the left in-ear headphone 504(1) and as discussed with respect to FIGS. 4A-4F.

The housings 506(1), 506(2) of the left and right in-ear headphones 504(1), 504(2) may be in the shape of a standard pair of wireless in-ear headphones and may be made of plastic, rubber, and/or metal materials, etc. The wires coming from the left and right in-ear headphone tip 508(1), 508(2) may be soldered onto or otherwise electrically connected with printed circuit boards or other electrical components in the left and right housings.

The electronic device 502 of the in-ear headphone pair 500 is in electronic communication with the left in-ear headphone 504(1), where the electronic communication could be wired or wireless (e.g., Bluetooth). It is anticipated that when the left and right in-ear headphones 504(1), 504(2) are wired, the wired connection can assist users in orienting the left in-ear headphone 504(1) for top-bottom stimulation, as discussed above. The left in-ear housing 506(1) may include a portion that extends over the ear of a user and may include batteries therein, such as for a wireless configuration. Similarly, the right in-ear housing 506(2) may include a portion that extends over the ear of the user and may include batteries therein, such as for a wireless configuration. In this way, the in-ear headphone pair 500 may be used as a traditional wireless pair of headphones controlled by a wireless application (e.g., mobile application, smartphone application, etc.) of an electronic device (e.g., laptop, smartphone, etc.) external to the in-ear headphone pair 500, but with the additional ability to stimulate the vagus nerve. In particular, the left and right in-ear headphones 504(1), 504(2) may include wireless communication components, such as a signal transmitter and/or a signal receiver for wireless communication with the electronic device 502.

The electronic device 502 of the in-ear headphone pair 500 controls operation of the electrical stimulation components 510 and/or the audio stimulation components 512(1), 512(2). In this way, a user can receive simultaneous or concurrent electrical stimulation (of the vagus nerve) and audio stimulation (e.g., music). In other words, for example, the left in-ear headphone 504(1) provides electric stimulation of the vagus nerve while simultaneously allowing audio to be transmitted through the in-ear headphone tip 508(1). The electronic device 502 (e.g., smartphone, laptop, etc.) can control or modify the electrical stimulation components 510 including stimulation intensity, duration, pulsing pattern, length of session, and/or audio controls, among other operating parameters. Each of the left and right in-ear headphones 504(1), 504(2) may include a power button to turn on and off the left and right in-ear headphones 504(1), 504(2).

Figure 6:
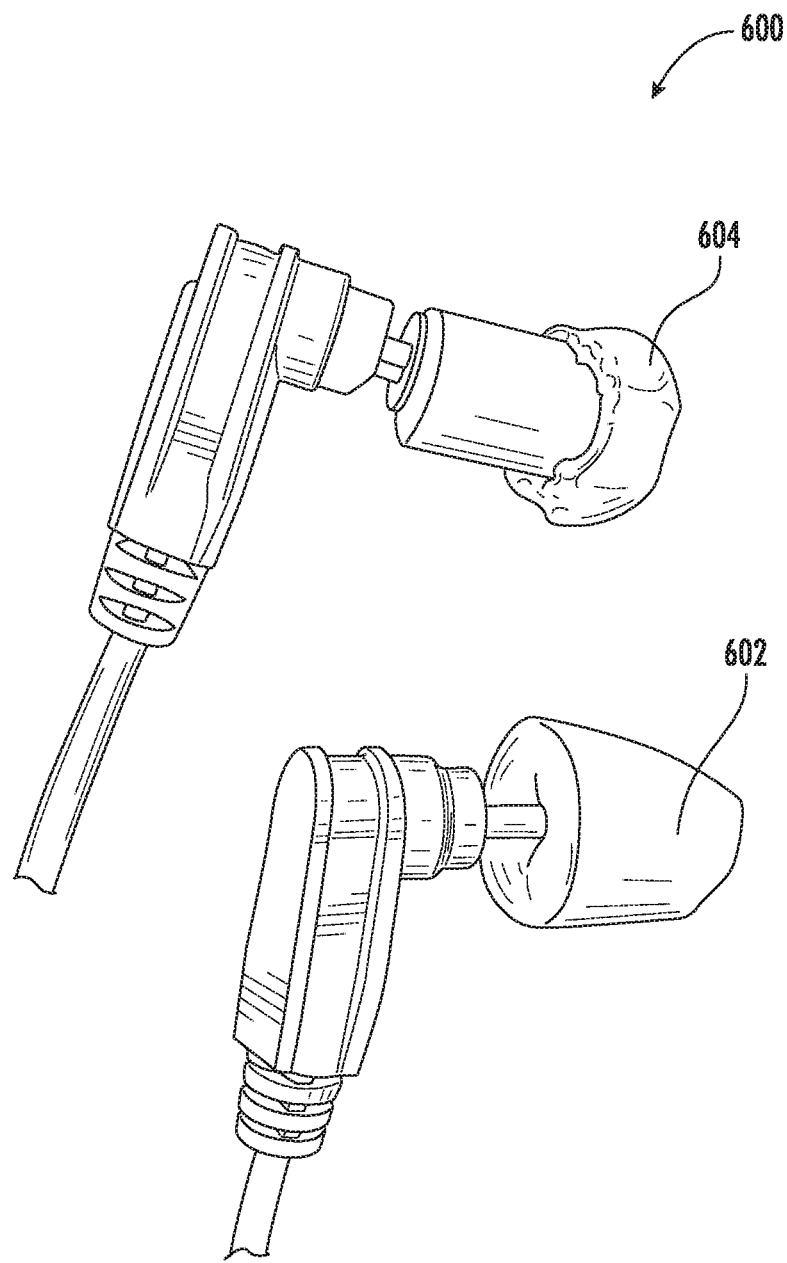
FIG. 6 is a perspective view of another embodiment of a stimulation electrode assembly with the in-ear headphone tip of FIG. 5 and with a return path electrode assembly.

FIG. 6 is a perspective view of another embodiment of a stimulation electrode assembly 600 with an in-ear headphone tip 602 (may also be referred to as a stimulation electrode, contact electrode, etc.) and with a return path electrode assembly 604. In this embodiment, the stimulation electrode 602 is generally frustoconical (as discussed above) for insertion into the ear canal of the ear. The stimulation electrode 602 can include a conductive gel coated on an outer surface thereof. The return path contact electrode 604 may also include a conductive gel coated on an outer surface thereof. When the stimulation electrode 602 is inserted into the ear, the return path contact electrode 604 is positioned at some other point on the body (e.g., ear, neck, chest, etc.) to form an electrical circuit, thereby allowing the stimulation electrode 602 to stimulate the vagus nerve of a user. The more surface area in contact with the stimulation electrode 602 and the more pressure applied, the more current flows out of the stimulation electrode 602.

Figure 7:
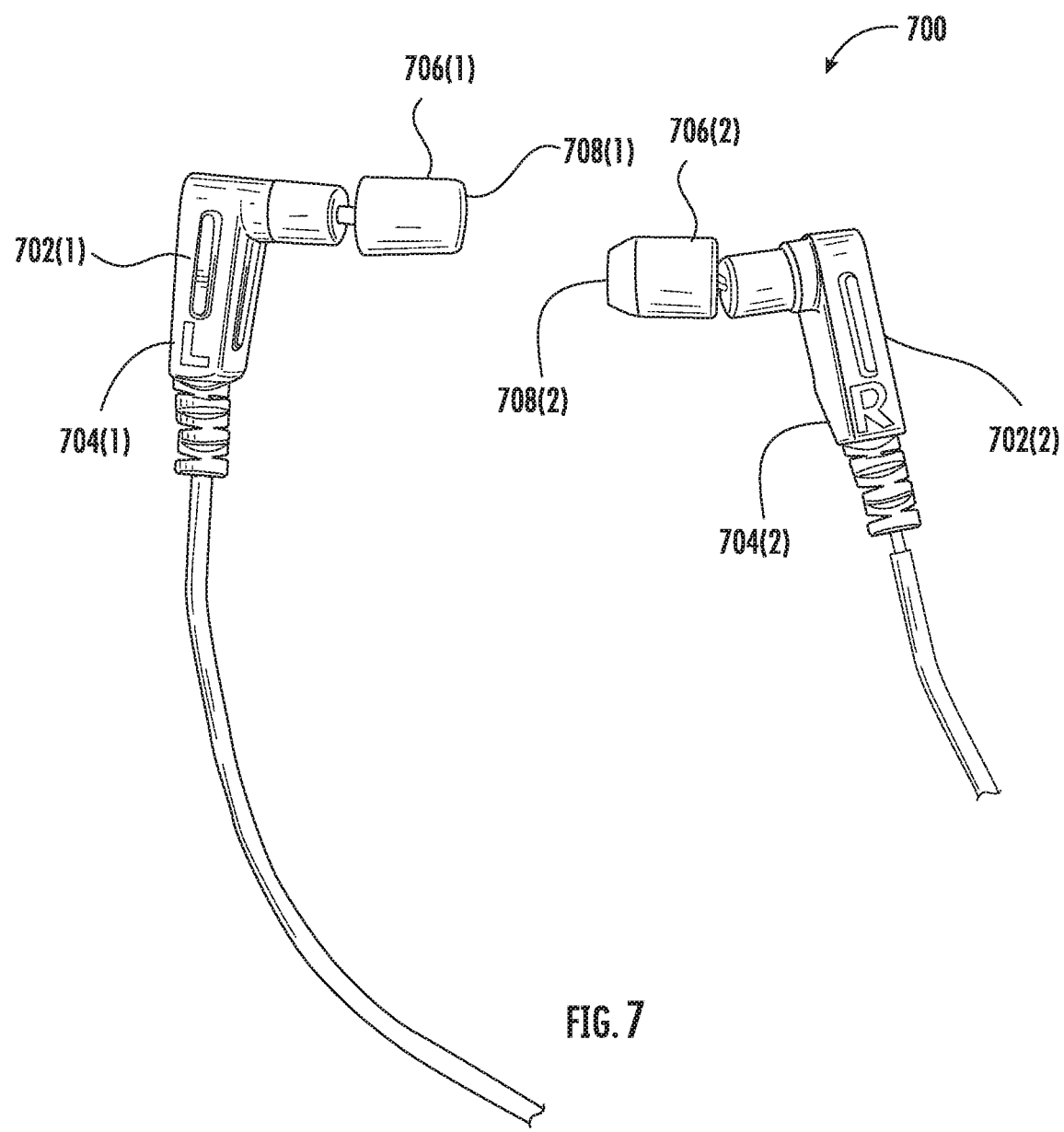
FIG. 7 is a perspective view of another embodiment of an in-ear headphone pair for non-invasive vagus nerve stimulation.

FIG. 7 is a perspective view of another embodiment of an in-ear headphone pair 700 for non-invasive vagus nerve stimulation. The in-ear headphone pair 700 includes an electronic device (see e.g., FIG. 8 below), a left in-ear headphone 702(1) (e.g., first in-ear headphone), and a right in-ear headphone 702(2) (e.g., second in-ear headphone).

The left in-ear headphone 702(1) includes a left housing 704(1) and a left in-ear headphone tip 706(1) including a first electrode 708(1) (e.g., anode or cathode) of a generally frustoconical-shape. The left in-ear headphone tip 706(1) defines a left central channel (see FIGS. 4A-4F). The right in-ear headphone 702(2) includes a right housing 704(2) and a right in-ear headphone tip 706(2) including a second electrode 708(2) (e.g., cathode or anode) of a generally frustoconical-shape. The right in-ear headphone tip 706(2) defines a right central channel (see FIGS. 4A-4F). When the left in-ear headphone tip 706(1) is positioned in the left ear of a user and the right in-ear headphone tip 706(2) is positioned in the right ear of the user, an electrical circuit is created from the first electrode 708(1) of the left in-ear headphone 702(1) through skin tissue of the left ear, through the vagus nerve, across the user's skin, through skin tissue of the right ear, and to the second electrode 708(2) of the right in-ear headphone 702(2). In this way, the in-ear headphone pair 700 non-invasively stimulates the vagus nerve of the user, and may be produced by a simplified the manufacturing process. It is noted that the vagus nerve will be stimulated regardless of whether the left in-ear headphone is placed in the left ear or the right ear.

In certain embodiments, one or both of the first electrode 708(1) and the second electrode 708(2) include a conductive material, such as conductive silver and/or conductive silicone (e.g., carbon-filled silicone, silver-filled silicone, etc.). In certain embodiments, the first electrode 708(1) and/or the second electrode 708(2) (either one or both) include a conductive gel (e.g., hydrogel) applied to the outer surface of the first electrode 708(1) and the second electrode 708(2) to maximize contact with the skin in the ear canal and to increase current distribution for increased comfort of the user. In other embodiments, the first electrode 708(1) and the second electrode 708(2) are made (e.g., exclusively) of the conductive gel such that the conductive gel forms the frustoconical-shape of the first electrode 708(1) and the second electrode 708(2). Forming the first electrode 708(1) and/or the second electrode 708(2) from the conductive gel (e.g., devoid of silver and/or silicon) simplifies the manufacturing process without sacrificing performance or comfort.

In certain embodiments, the first electrode 708(1) and/or the second electrode 708(2) do not include a central channel, and the in-ear headphone pair 700 is configured to deliver electrical stimulation only (not audio stimulation).

FIG. 8 is a general diagram illustrating the in-ear headphone pair 700 of FIG. 7. The in-ear headphone pair 800 includes an electronic device 802, a left in-ear headphone 804(1), and a right in-ear headphone 804(2).

As discussed above, the left in-ear headphone 804(1) includes a housing 806(1) and a left in-ear headphone tip 808(1) with electrical stimulation components 810(1) and audio stimulation components 812(1) positioned within the left in-ear headphone housing 806(1). The right in-ear headphone 804(2) includes a housing 806(2) and a right in-ear headphone tip 808(2) with electrical stimulation components 810(2) and audio stimulation components 812(2) positioned within the housing 806(2).

The left and/or right in-ear headphones 804(1), 804(2) have the same form as a conventional in-ear headphone seen on a consumer pair of in-ear headphones. The left and/or right in-ear headphone housings 806(1), 806(2) of the left and right in-ear headphones 804(1), 804(2) each include electrical stimulation components 810(1), 810(2) and audio stimulation components 812(1), 812(2). The electrical stimulation components 810(1), 810(2) include a waveform generator (e.g., left waveform generator and/or right waveform generator) to provide the electrical stimulation parameters. The waveform generator may be configured to deliver a biphasic waveform (e.g., periodically altering the direction of current between the first electrode and the second electrode by periodically flipping polarity). The stimulation waveform parameters can produce an output of 0-20 mA at a frequency of 0-1 MHz and pulse width of 0-1000 us. The audio stimulation components 812(1), 812(2) include a speaker. In particular, it is anticipated that at least a portion of the left housing 806(1) may be inserted into the left central channel (see FIGS. 4A-4F) of the left in-ear headphone tip 808(1) to attach the left housing 806(1) and the left in-ear headphone tip 808(1) to each other, such that the audio components 812(1) positioned within the left housing 806(1) can deliver audio stimulation to the left ear through the left central channel of the first electrode of the left in-ear headphone tip 808(1). Similarly, at least a portion of the right housing 806(2) may be inserted into the right central channel (see FIGS. 4A-4F) to attach the right housing 806(2) and the right in-ear headphone tip 808(2) to each other, such that the audio components 812(2) positioned within the right housing 806(2) can deliver audio stimulation to the right ear through the right central channel of the second electrode of the right in-ear headphone tip 808(2).

The housings 806(1), 806(2) of the left and/or right in-ear headphones 804(1), 804(2) may be in the shape of a standard pair of wireless in-ear headphones and may be made of plastic, rubber, and/or metal materials, etc. The wires coming from the left and right in-ear headphone tips 808(1), 808(2) may be soldered onto or otherwise electrically connected to a printed circuit board or other electrical components in the left and right housings 806(1), 806(2).

The electronic device 802 is in electronic communication with the left and/or right in-ear headphone 804(1), 804(2), where the electronic communication could be wired or wireless (e.g., Bluetooth). It is anticipated that when the left and right in-ear headphones 804(1), 804(2) are wired, the wired connection can assist users in orienting the left in-ear headphone tip 808(1) for top-bottom stimulation, as discussed above. The left and/or right in-ear housing 806(1), 806(2) may include a portion that extends over the ear and may include batteries therein, such as for a wireless configuration. In this way, the in-ear headphone pair 800 may be used as a traditional wireless pair of headphones controlled by a wireless application (e.g., mobile application, smartphone application, etc.) of an electronic device 802 (e.g., laptop, smartphone, etc.) external to the in-ear headphone pair 800, but with the additional ability to stimulate the vagus nerve of a user. In particular, the left and right in-ear headphones 804(1), 804(2) may include wireless communication components, such as a signal transmitter and/or a signal receiver for wireless communication with the electronic device 802.

The electronic device 802 controls operation of the electrical stimulation components 810(1), 810(2) and/or the audio stimulation components 812(1), 812(2) of the left and/or right in-ear headphone 804(1), 804(2). In this way, a user can receive simultaneous or concurrent electrical stimulation (of the vagus nerve) and audio stimulation (e.g., music) in the left and/or right ears. In other words, the left and right in-ear headphone tips 808(1), 808(2) provide electric stimulation of the vagus nerve while simultaneously allowing audio to be transmitted through the left and/or right in-ear headphone tip 808(1), 808(2). The electronic device 802 (e.g., smartphone, laptop, etc.) can control or modify the electrical stimulation components 810(1), 810(2) including stimulation intensity, duration, pulsing pattern, length of session, and/or audio controls, among other operating parameters. Each of the left and right in-ear headphones 804(1), 804(2) may include a power button to turn on and off the left and right in-ear headphones 804(1), 804(2).

It is contemplated that any or more features or characteristics of any one or more embodiments disclosed herein may be combined with those of other embodiments, unless specifically indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. An electrode assembly for non-invasive nerve stimulation, comprising:
    a first electrode forming a first body;
    a second electrode forming a second body complementary to the first body such that the first body of the first electrode and the second body of the second electrode in combination form a frustoconical-shape; and
    a shim positioned between the first electrode and the second electrode to separate and electrically insulate the first electrode and the second electrode from each other;
    wherein the electrode assembly is configured for insertion into an ear of a user to form an electrical circuit including the first electrode, the second electrode, and a vagus nerve of the user to electrically stimulate the vagus nerve;
    wherein the electrode assembly is coupled with a waveform generator configured to deliver a biphasic waveform between the first electrode and the second electrode.

2. The electrode assembly of claim 1, wherein the first electrode and the second electrode comprise conductive silicone.

3. The electrode assembly of claim 1, wherein the shim comprises a plastic material.

4. The electrode assembly of claim 1, further comprising a conductive gel covering at least a portion of an outer surface of at least one of the first electrode or the second electrode.

5. The electrode assembly of claim 4, wherein the conductive gel comprises a hydrogel.

6. The electrode assembly of claim 4, wherein:
    the shim comprises a ridge that extends beyond the outer surface of the first electrode and the second electrode;
    the conductive gel comprises a first gel portion covering at least a portion of the first electrode and a second gel portion covering at least a portion of the second electrode; and
    the first gel portion and the second gel portion are electrically insulated from each other by the ridge.

7. The electrode assembly of claim 1, wherein the first electrode and the second electrode are substantially a same size and the shim is positioned in an approximate middle of the electrode assembly.

8. The electrode assembly of claim 1, wherein the first electrode and the second electrode are differently sized and the shim is positioned offset from a middle of the electrode assembly.

9. An in-ear headphone, comprising:
    a housing;
    an electrode assembly forming an in-ear headphone tip attached to the housing, the electrode assembly comprising:
        a first electrode forming a first body;
        a second electrode forming a second body complementary to the first body such that the first body of the first electrode and the second body of the second electrode in combination form a frustoconical-shape; and
        a shim positioned between the first electrode and the second electrode to separate and electrically insulate the first electrode and the second electrode from each other;
        wherein the electrode assembly is configured for insertion into an ear of a user to form an electrical circuit including the first electrode, the second electrode, and a vagus nerve of the user to electrically stimulate the vagus nerve; and
    a waveform generator positioned within the housing and configured to apply an electric signal to the electrode assembly to stimulate the vagus nerve, wherein the waveform generator configured to deliver a biphasic waveform between the first electrode and the second electrode.

10. The in-ear headphone of claim 9, wherein the first electrode and the second electrode comprise conductive silicone.

11. The in-ear headphone of claim 9, wherein the shim comprises a plastic material.

12. The in-ear headphone of claim 9, further comprising a conductive gel covering at least a portion of an outer surface of at least one of the first electrode or the second electrode.

13. The in-ear headphone of claim 9, wherein the in-ear headphone comprises a signal transmitter and a signal receiver configured to permit wireless communication with an electronic device external to the in-ear headphone.

14. The in-ear headphone of claim 9, wherein the in-ear headphone is configured to allow a user to adjust an operating parameter of the waveform generator by an electronic device, the operating parameter comprising at least one of intensity, duration, or pulse pattern.

15. The in-ear headphone of claim 9, wherein the in-ear headphone comprises audio components within the housing, the audio components configured to deliver audio stimulation through a central channel defined in the electrode assembly, the in-ear headphone configured to provide the audio stimulation concurrently with electrical stimulation of the vagus nerve.

16. An in-ear headphone pair, comprising:
    a right in-ear headphone configured for insertion into a right ear, the right in-ear headphone comprising audio components configured to deliver audio stimulation to the right ear; and
    a left in-ear headphone configured for insertion into a left ear, the left in-ear headphone comprising:
        a housing;
        an electrode assembly forming an in-ear headphone tip attached to the housing, the electrode assembly comprising:
            a first electrode forming a first body;
            a second electrode forming a second body complementary to the first body such that the first body of the first electrode and the second body of the second electrode in combination form a frustoconical-shape; and a shim positioned between the first electrode and the second electrode to separate and electrically insulate the first electrode and the second electrode from each other;

wherein the electrode assembly is configured for insertion into an ear of a user to form an electrical circuit including the first electrode, the second electrode, and a vagus nerve of the user to electrically stimulate the vagus nerve;

a waveform generator positioned within the housing and configured to apply an electrical signal to the electrode assembly to stimulate the vagus nerve, wherein the waveform generator configured to deliver a biphasic waveform between the first electrode and the second electrode; and audio components positioned within the housing and configured to deliver audio stimulation to the left ear through a central channel of the electrode assembly.

17. The in-ear headphone pair of claim 16, wherein the first electrode and the second electrode comprise conductive silicone.

18. The in-ear headphone pair of claim 16, wherein the shim comprises a plastic material.

19. The in-ear headphone pair of claim 16, further comprising a conductive gel covering at least a portion of an outer surface of at least one of the first electrode or the second electrode.

20. The in-ear headphone pair of claim 16, wherein the in-ear headphone pair comprises a signal transmitter and a signal receiver configured to permit wireless communication with an electronic device external to the in-ear headphone pair.

21. The in-ear headphone pair of claim 16, wherein the left in-ear headphone is configured to deliver the audio stimulation concurrently with electrical stimulation.

* * * * *